(12) United States Patent
Wang (10) Patent No.: US 12,270,125 B2
(45) Date of Patent: Apr. 8, 2025

(54) SYSTEM AND METHOD FOR MODULAR AND COMBINATORIAL NUCLEIC ACID SAMPLE PREPARATION FOR SEQUENCING

(71) Applicant: Roche Sequencing Solutions, Inc., Pleasanton, CA (US)

(72) Inventor: Alexandra Hui Wang, Mountain View, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1036 days.

(21) Appl. No.: 17/278,463

(22) PCT Filed: Sep. 19, 2019

(86) PCT No.: PCT/EP2019/075144
§ 371 (c)(1),
(2) Date: Mar. 22, 2021

(87) PCT Pub. No.: WO2020/058389
PCT Pub. Date: Mar. 26, 2020

(65) Prior Publication Data
US 2022/0033806 A1     Feb. 3, 2022

Related U.S. Application Data (60) Provisional application No. 62/734,809, filed on Sep. 21, 2018.

(51) Int. Cl.
| | | |
|---|---|---|
| C40B 50/06 | (2006.01) | |
| C12N 15/10 | (2006.01) | |
| C12Q 1/6869 | (2018.01) | |

(52) U.S. Cl.
CPC .......... *C40B 50/06* (2013.01); *C12N 15/1065* (2013.01); *C12Q 1/6869* (2013.01)

(58) Field of Classification Search
None
See application file for complete search history.

(56) References Cited

U.S. PATENT DOCUMENTS

| | | |
|---|---|---|
| 2017/0211140 A1 | 6/2017 | Schmitt et al. |
| 2018/0100145 A1 | 4/2018 | Lau et al. |

FOREIGN PATENT DOCUMENTS

| | | |
|---|---|---|
| WO | 2005/080604 A2 | 9/2005 |
| WO | 2015/100427 A1 | 7/2015 |

(Continued)

OTHER PUBLICATIONS

Faircloth, Brant C.; Glenn, Travis C., Not all Sequence Tags Are Created Equal: Designing and Validating Sequence Identification Tags Robust to Indels, PLOS One, (2012), pp. e42543, vol. 7 Issue 8.

(Continued)

*Primary Examiner* — Christian C Boesen
(74) *Attorney, Agent, or Firm* — Eric Grant Lee (57) ABSTRACT

The present disclosure provides a method of preparing a library of nucleic acids having modular end sequences. The method includes combining a pool of different modular nucleic acid tags with a nucleic acid sample, the nucleic acid sample including a plurality of double-stranded target nucleic acids. The method further includes joining the ends of each of the double-stranded target nucleic acids to tags selected from the pool of different modular nucleic acid tags to form a plurality of doubly-tagged target nucleic acids, amplifying each of the doubly-tagged target nucleic acids, thereby preparing a library of nucleic acids having modular end sequences, and detecting the library of amplified nucleic acids having modular end sequences.

11 Claims, 2 Drawing Sheets
Specification includes a Sequence Listing.

(56) References Cited

FOREIGN PATENT DOCUMENTS

| | | |
|---|---|---|
| WO | 2016168351 A1 | 10/2016 |
| WO | 2017100441 A1 | 6/2017 |
| WO | 2018/108328 A1 | 6/2018 |

OTHER PUBLICATIONS

International Search Report and Written Opinion for PCT/EP19/75144 filed Sep. 19, 2019, Issued Dec. 5, 2019.

SYSTEM AND METHOD FOR MODULAR AND COMBINATORIAL NUCLEIC ACID SAMPLE PREPARATION FOR SEQUENCING

BACKGROUND

The disclosure relates, in general, to the field of nucleic acid analysis and, more particularly, to preparing templates for nucleic acid sequencing.

Single molecule nucleic acid sequencing workflows generally include a step of preparing a library of target molecules that is compatible for analysis with the selected sequencing technology. While a variety of library preparation schemes exist, many of these schemes are limited to samples or sequencing instruments of a particular type. Accordingly, there is a need for improved library preparation schemes that are applicable to a wide variety of sample types and sequencing systems.

SUMMARY

The present invention overcomes the aforementioned drawbacks by providing a system and method for nucleic acid sample preparation for sequencing.

In accordance with one embodiment of the present disclosure, a method of preparing a library of nucleic acids having modular end sequences includes combining a pool of different modular nucleic acid tags with a nucleic acid sample, the nucleic acid sample including a plurality of double-stranded target nucleic acids. The method further includes joining the ends of each of the double-stranded target nucleic acids to tags selected from the pool of different modular nucleic acid tags to form a plurality of doubly-tagged target nucleic acids, amplifying each of the doubly-tagged target nucleic acids, thereby preparing a library of nucleic acids having modular end sequences, and detecting the library of amplified nucleic acids having modular end sequences. Each of the different modular nucleic acid tags has a first strand and a second strand. The first strand includes i) a segment A defining a 5' end of the first strand, and ii) a segment B defining a 3' end of the first strand. The second strand includes i) a segment B' defining a 5' end of the second strand and complementary to the segment B of the first strand, and ii) a segment A' defining a 3' end of the second strand and complementary to the segment A of the first strand. Each of different modular nucleic acid tags optionally includes a segment C, the segment C positioned intermediate one of i) the segment A and the segment B, and ii) the segment A' and the segment B'. Each of the segments A, A', B, B', and C are selected from a set of segments having different nucleic acid sequences. Each segment of the set of segments has a defined sequence of at least 10 nucleotides, and the set of segments is characterized by a pairwise edit distance of at least 3.

In one aspect, each of the different modular nucleic acid tags comprises the segment C on one of the first strand and the second strand.

In another aspect, each of the different modular nucleic acid tags comprises the segment C on each of the first strand and the second strand.

In another aspect, the segment C comprises a hairpin.

In another aspect, the hairpin comprises a stem region and a loop region.

In another aspect, each of the different modular nucleic acid tags further includes at least one strand cleavage site.

In another aspect, the method further includes contacting the doubly-tagged target nucleic acids with a cleavage agent to cleave the doubly-tagged target nucleic acid at the cleavage sites, thereby forming cleaved doubly-adapted target nucleic acids.

In another aspect, the method further includes concatenating the doubly-tagged target nucleic acids, thereby forming concatenated doubly-tagged target nucleic acids.

In another aspect, the method further includes joining the ends of each of the concatenated doubly-tagged target nucleic acids with an adapter, thereby forming a plurality of doubly-adapted concatemers.

In another aspect, the method further includes amplifying each of the doubly-adapted concatemers.

In another aspect, joining to the modular nucleic acid tag is by ligation.

In another aspect, the ligation is by joining of cohesive ends of the target nucleic acid and the modular nucleic acid tag.

In another aspect, the cleavage site includes one or more deoxyuracils and the cleavage agent includes Uracil-DNA-N-glycosylase (UNG) and an endonuclease.

In another aspect, the endonuclease is selected from Endonuclease III, Endonuclease IV, and Endonuclease VIII.

In another aspect, the cleavage site includes one or more abasic sites and the cleavage agent includes an endonuclease selected from Endonuclease III, Endonuclease IV, and Endonuclease VIII.

In another aspect, the modular nucleic acid tag includes a nuclease protection nucleotide.

In another aspect, the nuclease protection nucleotide contains a phosphorothioate group.

In another aspect, each of the different modular nucleic acid tags further includes a punctuation sequence, the punctuation sequence including at least three blocks, each of the blocks consisting of a homopolymer of at least three identical nucleotides.

In another aspect, each of the different modular nucleic acid tags further includes at least one of a sample identifier sequence and a molecular identifier sequence.

In another aspect, the step of joining is targeted.

In another aspect, the joining is non-targeted.

In another aspect, the method further includes sequencing the library of amplified nucleic acids having modular end sequences, thereby generating a plurality of sequencing reads, and analyzing the plurality of sequencing reads by at least one of i) deduplicating the plurality of sequencing reads, and ii) determining a consensus sequence.

In accordance with another embodiment of the present disclosure, a composition includes a pool of modular nucleic acid tags. Each of the tags includes a first strand including i) a segment A defining a 5' end of the first strand, and ii) a segment B defining a 3' end of the first strand, and a second strand including i) a segment B' defining a 5' end of the second strand and complementary to the segment B of the first strand, and ii) a segment A' defining a 3' end of the second strand and complementary to the segment A of the first strand. Each of modular nucleic acid tags optionally includes a segment C, the segment C positioned intermediate one of i) the segment A and the segment B, and ii) the segment A' and the segment B'. Each of the segments A, A', B, B', and C are selected from a set of segments having different nucleic acid sequences. Each segment of the set of segments has a defined sequence of at least 10 nucleotides, and the set of segments is characterized by a pairwise edit distance of at least 3.

In one aspect, each of the modular nucleic acid tags comprises the segment C on one of the first strand and the second strand.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

I. Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Adapter: As used herein, the term "adapter" means a nucleotide sequence that may be added to another sequence so as to import additional properties to that sequence. An adapter is typically an oligonucleotide that can be single- or double-stranded, or may have both a single-stranded portion and a double-stranded portion. The term "adapted target nucleic acid" refers to a nucleic acid to which an adapter is conjugated at one or both ends. Other terms used interchangeably for adapter herein are "tag" and "cap".

Amplification: As used herein, the term "amplification" refers to a process of making additional copies of the target nucleic acid. Amplification can have more than one cycle, e.g., multiple cycles of exponential amplification. Amplification may have only one cycle (making a single copy of the target nucleic acid). The copy may have additional sequences, e.g., those present in the primers used for amplification. Amplification may also produce copies of only one strand (linear amplification) or preferentially one strand (asymmetric PCR).

Approximately: As used herein, the term "approximately" or "about", as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level, and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Barcode: As used herein, the term "barcode" refers to a nucleic acid sequence that can be detected and identified. Barcodes can be incorporated into various nucleic acids. Barcodes are sufficiently long e.g., 2, 5, 20 nucleotides, so that in a sample, the nucleic acids incorporating the barcodes can be distinguished or grouped according to the barcodes.

Biological Sample: As used herein, the term "biological sample" typically refers to a sample obtained or derived from a biological source (e.g., a tissue or organism or cell culture) of interest, as described herein. In some embodiments, a source of interest comprises or consists of an organism, such as an animal or human. In some embodiments, a biological sample comprises or consists of biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample comprises or consists of cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Combinatorial: As used herein, the term "combinatorial" is given its ordinary meaning (i.e., of, relating to, or involving combinations). Accordingly, a composition described as "combinatorial" indicates that the composition is composed from a selection of discrete elements belonging to finite sets. A combinatorial set includes all elements that satisfy a certain given criteria. For instance, a pool of combinatorial nucleic acid tags includes tags composed of a finite set of defined nucleic acid sequences and arranged in a defined order. In one example, a combinatorial nucleic acid tag can be composed of an element A, an element B, and an element C in the order A-B-C, where the element A is selected from a first finite set of different nucleic acids, the element B is selected from a second finite set of different nucleic acids, and the element C is selected from a third finite set of different nucleic acids. A method described as combinatorial indicates that the method is comprised of one or more steps or workflows selected from a finite set of steps or workflows.

Comprising: A composition or method described herein as "comprising" one or more named elements or steps is open-ended, meaning that the named elements or steps are essential, but other elements or steps may be added within the scope of the composition or method. It is to be understood that composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Designed: As used herein, the term "designed" refers to an agent (i) whose structure is or was selected by the hand of man; (ii) that is produced by a process requiring the hand of man; and/or (iii) that is distinct from natural substances and other known agents.

Determine: Those of ordinary skill in the art, reading the present specification, will appreciate that "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Ligation: As used herein, the term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

Modified Nucleotide: As used herein, the term "modified nucleotide" describes a nucleotide in DNA with a base other than the four conventional DNA bases consisting of adenosine, guanosine, thymidine, and cytosine. The nucleotides dA, dG, dC, and dT are conventional. However, deoxyuracil (dU) and deoxyinosine (dI) are modified nucleotides in DNA. Ribonucleotides (rA, rC, rU and rG) inserted into DNA are also considered "modified nucleotides" in the context of the present invention. Finally, non-nucleotide moieties (such as PEG) inserted in place of nucleotides into a nucleic acid strand are also considered "modified nucleotides" in the context of the present invention. Nucleotides can be further modified in yet other ways, such as through the inclusion of non-natural linkages, including phosphorothioate linkages.

Multiplex Identifier: As used herein, the term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated. Another term for MID that may be used interchangeable is "sample identifier" or "SID".

Nucleic acid: As used herein, the term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil, and thymidine) as well as non-natural bases. Some examples of non-natural bases include those described in, e.g., Seela et al., (1999) Helv. Chim. Acta 82:1640. The non-natural bases may have a particular function, e.g., increasing the stability of the nucleic acid duplex, inhibiting nuclease digestion or blocking primer extension or strand polymerization.

Polynucleotide and Oligonucleotide: As used herein, the terms "polynucleotide" and "oligonucleotide" are used interchangeably. Polynucleotide is a single-stranded or a double-stranded nucleic acid. Oligonucleotide is a term sometimes used to describe a shorter polynucleotide. Oligonucleotides are prepared by any suitable method known in the art, for example, by a method involving direct chemical synthesis as described in Narang et al. (1979) Meth. Enzymol. 68:90-99; Brown et al. (1979) Meth. Enzymol. 68:109-151; Beaucage et al. (1981) Tetrahedron Lett. 22:1859-1862; Matteucci et al. (1981) J. Am. Chem. Soc. 103:3185-3191.

Primer: As used herein, the term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

Sample: As used herein, the term "sample" refers to any composition containing or presumed to contain one or more target nucleic acids. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

Self-priming adapter: As used herein, the term "self-priming adapter" refers to an adapter capable of initiating strand extension (copying of the strand) from the adapter itself. The self-priming adapter is contrasted with a traditional adapter comprising a primer binding site where a separate primer molecule binds to the adapter to initiate strand extension from the primer.

Sequencing: As used herein, the term "sequencing" refers to any method of determining the sequence of nucleotides in the target nucleic acid.

Single-Pass Accuracy: As used herein, the term "single-pass accuracy" refers to the accuracy of the output data (e.g., individual base calls) determined by the sequencing platform resulting from a single-pass over a given template and prior to the assembly of a consensus sequence, if applicable. In the case of a sequencing-by-synthesis reaction, a single-pass would involve the replication of a single copy of the template. In the case of single-molecule sequencing platforms based on the passage of a single molecule through a pore or other like channel, a single-pass would involve the singular passage of the molecule through the channel.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Synthetic: As used herein, the term "synthetic" means produced by the hand of man, and therefore in a form that does not exist in nature, either because it has a structure that does not exist in nature, or because it is either associated with one or more other components, with which it is not associated in nature, or not associated with one or more other components with which it is associated in nature.

Target Sequence: As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

Unique Molecular Identifier: As used herein, the term "unique molecular identifier" or "UID" refers to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

Universal Primer: As used herein, the terms "universal primer" and "universal priming binding site" or "universal priming site" refer to a primer and primer binding site present in (typically, through in vitro addition to) different target nucleic acids. The universal priming site is added to the plurality of target nucleic acids using adapters or using target-specific (non-universal) primers having the universal priming site in the 5'-portion. The universal primer can bind to and direct primer extension from the universal priming site.

More generally, the term "universal" refers to a nucleic acid molecule (e.g., primer or other oligonucleotide) that can be added to any target nucleic acid and perform its function irrespectively of the target nucleic acid sequence. The universal molecule may perform its function by hybridizing to the complement, e.g., a universal primer to a universal primer binding site or a universal circularization oligonucleotide to a universal primer sequence.

II. Detailed Description of Certain Embodiments

As also discussed above, in various situations it may be useful to provide a method for nucleic acid sample preparation for sequencing. As would be appreciated by one of ordinary skill in the art, the design of a given nucleic acid sequencing platform dictates the types and configurations of nucleic acids that can be sequenced. Accordingly, in order to use a sequencing platform, it is generally required that nucleic acids present in a sample first be manipulated to provide the nucleic acids in a format that is compatible with the sequencing platform. Typical sample preparation workflow require steps such as isolation of the nucleic acids away from the rest of sample, conversion of the nucleic acids into double-stranded molecules (typically double-stranded DNA), fragmentation of the nucleic acids into molecules having a uniform, defined length or length distribution, and modification of the termini of the nucleic acids with nucleic acid adapters.

The application of adapters in nucleic acid sample preparation is of particular importance for sequencing as these adapters may optionally include such features as priming sites, universal identifier sequences (UID) also known as barcodes, and sample identifier sequences (SID) also known as sample indices and multiplex identifier sequences (MID).

One challenge associated with existing methods for nucleic acid sample preparation for sequencing is that the methods are not universally applicable for either the sample type or the sequencing platform. That is, existing workflows are most often specific for a particular sample type and a specific sequencing platform. Moreover, these workflows are often divergent or incompatible with one another. As a result, a user must learn a wide variety of different workflows and obtain a wide variety of reagents and equipment in the case that it is desirable to work with different sample types or sequencing platforms.

These and other challenges may be overcome with a system and method for modular and combinatorial nucleic acid sample preparation for sequencing according to the present disclosure. In one aspect, the present disclosure provides for a set of compatible sample preparation steps and workflows that may be mixed and matched to in order to accommodate a wide variety of sample types and sequencing platforms. The following description describes each of these novel steps and workflows individually, and then illustrates examples of how these steps and workflows may be combined according to the present disclosure.

As discussed above, single molecule sequencing methods involve a step of generating a library of adapted target nucleic acids. In some methods, the library is made of linear target nucleic acids. During a linear library preparation workflow, it may be desirable to associate individual library fragments with one or more UID, one or more SID, the like, or a combination thereof. Current approaches typically incorporate such identifier sequences into a universal adapter sequence that is appended to one or both ends of a target nucleic acid fragments to provide adapted library fragments. In one aspect, such adapters may limit downstream manipulations of the library fragments. In another aspect, such adapters may not be compatible with nucleic acids derived from a variety of sample types.

One aspect of the present disclosure provides for novel modular and combinatorial nucleic acid tags that are appended to one or both ends of a target nucleic acid fragment. The tags of the invention have numerous advantages. The tags facilitate the association of identifier sequences including, but not limited to, UID and SID with one or both ends of a target nucleic acid fragment. Tagged target nucleic acid fragments can then be further manipulated in a number of ways. In one example, tagged fragments can be concatenated together to form longer molecules suitable for long read sequencing approaches. In another example, tagged fragments can further be modified through the addition of nucleic acid adapters such as forked adapters or hairpin adapters.

The tags of the present disclosure are compatible with different types of target nucleic acids, including genomic DNA (gDNA), short fragments (i.e., less than about 200 nucleotides), long fragments (i.e., greater than about 200 nucleotides), nucleic acid amplification products, the like, and combinations thereof. The lengths of the target nucleic acids and the overall length of the finally prepared sequencing template compatible with the tags are limited only by the selected sequencing platform.

The tags of the present invention further facilitate detection of a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples), The sample may comprise whole blood or blood fractions where tumor cells may be present. In some embodiments, the sample, especially a liquid sample may comprise cell-free material such as cell-free DNA or RNA including cell-free tumor DNA or tumor RNA. The present invention is especially suitable for analyzing rare and low quantity targets. Further, the present invention can be modularized for both high abundance and low abundance samples. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus, or a mycoplasma.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism, including a single nucleotide polymorphism or variant (SNP or SNV), or a genetic rearrangement resulting e.g., in a gene fusion. In some embodiments, the target nucleic acid comprises a biomarker. In other embodiments, the target nucleic acid is characteristic of a particular organism, e.g., aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype. In yet other embodiments, all the sequences in the sample are target nucleic acids e.g., in shotgun genomic sequencing.

In an embodiment of the invention, a double-stranded target nucleic acid is converted into the template configuration of the invention. In some embodiments, the target nucleic acid occurs in nature in a single-stranded form (e.g., RNA, including mRNA, microRNA, viral RNA; or single-stranded viral DNA). The single-stranded target nucleic acid is converted into double-stranded form to enable the further steps of the claimed method.

Longer target nucleic acids may be fragmented although in some applications longer target nucleic acids may be desired to achieve a longer read. In some embodiments, the target nucleic acid is naturally fragmented, e.g., circulating cell-free DNA (cfDNA) or chemically degraded DNA such as the one founds in preserved samples. In other embodiments, the target nucleic acid is fragmented in vitro, e.g., by physical means such as sonication or by endonuclease digestion, e.g., restriction digestion.

In some embodiments, the invention comprises a target enrichment step. The enrichment may be by capturing the target sequences via one or more targets-specific probes. The nucleic acids in the sample may be denatured and contacted with single-stranded target-specific probes. The probes may comprise a ligand for an affinity capture moiety so that after hybridization complexes are formed, they are captured by providing the affinity capture moiety. In some embodiments, the affinity capture moiety is avidin or streptavidin and the ligand is biotin or desthiobiotin. In some embodiments, the moiety is bound to solid support. As described in further detail below, the solid support may comprise superparamagnetic spherical polymer particles such as DYNABEADS™ magnetic beads or magnetic glass particles.

In some embodiments of the present invention, adapter molecules are ligated to the target nucleic acid. The ligation can be a blunt-end ligation or a more efficient cohesive-end ligation. The target nucleic acid or the adapters may be rendered blunt-ended by "end repair" comprising strand-filling, i.e., extending a 3'-terminus by a DNA polymerase to eliminate a 5'-overhang. In some embodiments, the blunt-ended adapters and target nucleic acid may be rendered cohesive by addition of a single nucleotide to the 3'-end of the adapter and a single complementary nucleotide to the 3'-ends of the target nucleic acid, e.g., by a DNA polymerase or a terminal transferase. In yet other embodiments, the adapters and the target nucleic acid may acquire cohesive ends (overhangs) by digestion with restriction endonucleases. The latter option is more advantageous for known target sequences that are known to contain the restriction enzyme recognition site. In some embodiments, other enzymatic steps may be required to accomplish the ligation. In some embodiments, a polynucleotide kinase may be used to add 5'-phosphates to the target nucleic acid molecules and adapter molecules.

In some embodiments, the adapter molecules are in vitro synthesized artificial sequences. In other embodiments, the adapter molecules are in vitro synthesized naturally-occurring sequences. In yet other embodiments, the adapter molecules are isolated naturally occurring molecules.

In some embodiments, the invention comprises introduction of barcodes into the target nucleic acids by ligation of barcode-containing tags or adapters. Sequencing individual molecules typically requires molecular barcodes such as described e.g., in U.S. Pat. Nos. 7,393,665, 8,168,385, 8,481,292, 8,685,678, and 8,722,368. A unique molecular barcode is a short artificial sequence added to each molecule in a sample such as a patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy. See U.S. patent application Ser. Nos. 14/209,807 and 14/774,518. Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample. See Id.

In some embodiments of the present invention, adapters comprise one or more barcodes. A barcode can be a sample identifier (SID) or multiplex identifier sequence (MID) used to identify the source of the sample where samples are mixed (multiplexed). The barcode may also serve as a universal identifier sequence UID used to identify each original molecule and its progeny. The barcode may also be a combination of a UID and an MID. In some embodiments, a single barcode is used as both UID and MID.

In some embodiments, each barcode comprises a pre-defined sequence. In other embodiments, the barcode comprises a random sequence. Barcodes can be 1-40 nucleotides long.

In the method of the invention, the tag comprises a strand cleavage site. The cleavage site is selected from a modified nucleotide for which a specific endonuclease is available. A non-limiting list of examples of modified nucleotide-endonuclease pairs includes deoxyuracil—Uracil-N-DNA glycosylase (UNG) plus endonuclease; abasic site—AP nuclease; 8-oxoguanine-8-oxoguanine DNA glycosylase (also known as FPG (formamidopyrimidine [fapy]-DNA glycosylase)); deoxyinosine—alkyladenine glycosylase (AAG) plus endonuclease and ribonucleotide—RNaseH.

Different cleavage agents generate different products. In some embodiments, endonuclease VIII (Endo VIII) is used which creates a mixture of products, including 3'-P. In other embodiments, endonuclease III (Endo III) is used which creates a 3"-phospho-α,β-unsaturated aldehyde. In yet other embodiments, endonuclease IV (Endo IV) is used which creates a 3'-OH end. The non-extendable ends are advantageous in embodiments where a separate sequencing primer is used. An extendable 3'-end (3'-OH) is advantageous where there is no separate sequencing primer and the sequencing reaction is self-primed by the extendable 3'-end.

In some embodiments, the method includes a step of contacting the reaction mixture with an endonuclease capable of cleaving the cleavage site under the conditions where such cleavage could occur.

In some embodiments, the method includes affinity capture of the adapted target nucleic acids or any other sequencing intermediate (e.g., ternary complex of the pore protein, DNA polymerase and the template used in nanopore sequencing). To that end, the tags may incorporate an affinity ligand (e.g., biotin) that will enable the target to be captured by an affinity capture moiety (e.g., via streptavidin). In some embodiments, desthiobiotin is used. In some embodiments, the affinity capture utilizes the affinity molecule (e.g., streptavidin) bound to solid support. The solid support may be capable of suspension in a solution (e.g., a glass bead, a magnetic bead, a polymer bead or another like particle), or a solid-phase support (e.g., a silicon wafer, a glass slide, or the like). Examples of solution-phase supports include superparamagnetic spherical polymer particles such as DYNABEADS™ magnetic beads or magnetic glass particles such as described in U.S. Pat. Nos. 656,568, 6,274,386, 7,371,830, 6,870,047, 6,255,477, 6,746,874 and 6,258,531. In some embodiments, the affinity ligand is a nucleic acid sequence and its affinity molecule is a complementary sequence. In some embodiments, the solid substrate comprises a poly-T oligonucleotide while the tag comprises at least partially single-stranded poly-A portion.

In some embodiments, strand separation is enhanced by various agents selected from the single-strand binding protein, e.g., bacterial SSB, low complexity DNA C0t DNA (DNA enriched for repetitive sequences), or chemical agents such as alkali, glycerol, urea, DMSO or formamide.

In some embodiments, the invention comprises an exonuclease digestion step after the tag ligation step. The exonuclease may be a single strand-specific exonuclease, a double strand-specific exonuclease, or a combination thereof. The exonuclease may be one or more of Exonuclease I, Exonuclease III, and Exonuclease VII.

In some embodiments, the invention includes a method of making a library of sequencing-ready tagged target nucleic acids as described herein as well as the library produced by the method. Specifically, the library comprises a collection of tagged target nucleic acids derived from nucleic acids present in a sample. The tagged target nucleic acid molecules of the library comprise target sequences joined with tagged sequences at each end.

In some embodiments, the present invention comprises detecting target nucleic acids in a sample by nucleic acid sequencing. Multiple nucleic acids, including all the nucleic acids in a sample may be converted into the library of the invention and sequenced.

In some embodiments, the method further comprises a step of eliminating damaged or degraded targets from the library in order to improve the quality and length of sequencing reads. The step may comprise contacting the library with one or more of uracil DNA N-glycosylase (UNG or UDG), AP nuclease and FPG (formamidopyrimidine [fapy]-DNA glycosylase), also known as 8-oxoguanine DNA glycosylase in order to degrade such damaged target nucleic acids.

Sequencing can be performed by any method known in the art. Especially advantageous is the high-throughput single molecule sequencing capable of reading long target nucleic acids. Examples of such technologies include the Pacific Biosciences platform utilizing the SMRT (Pacific Biosciences, Menlo Park, Cal.) or a platform utilizing nanopore technology such as those manufactured by Oxford Nanopore Technologies (Oxford, UK) or Roche Sequencing Solutions (Roche Genia, Santa Clara, Cal.) and any other presently existing or future DNA sequencing technology that does or does not involve sequencing by synthesis. The sequencing step may utilize platform-specific sequencing primers.

In some embodiments, the sequencing step involves sequence analysis including a step of sequence aligning. In some embodiments, aligning is used to determine a consensus sequence from a plurality of sequences, e.g., a plurality having the same barcodes (UID). In some embodiments barcodes (UIDs) are used to determine a consensus from a plurality of sequences all having an identical barcode (UID). In other embodiments, barcodes (UIDs) are used to eliminate artifacts, i.e., variations existing in some but not all sequences having an identical barcode (UID). Such artifacts resulting from sample preparation or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

The present disclosure provide for the attachment of tags defining unique identification sequences (UID), sample identifier sequences (SID), or a combination thereof to one or both ends of dsDNA to be sequenced. These tags can be double-stranded nucleic acids composed of modular sequence segments/cassettes. Each segment can include a defined sequence on a first strand, and the complementary sequence on a second strand. Accordingly, tagging a both strands of a double-stranded target nucleic acid with the defined sequence (or the complementary sequence) provides for a combinatorial identifier as well as confirmation of the UID sequence data following the sequencing process. The resulting tagged double-stranded target nucleic acids can be directly attached to a sequencing adaptor or concatenated into long dsDNA. Each fragment with the resulting concatemers is separated (punctuated) on both ends with an identifier sequence, with the ends of the concatemers terminating in sequencing adapters. The tagged target nucleic acids can be further be amplified before or after concatenation, adaptor attachment, or both.

The disclosure describes a number of novel approaches for creating sequencing libraries suitable for use with, but not limited to long-read nucleic acid sequencing instruments. In one aspect, the disclosed methods are compatible with sequencing instruments that may be characterized by low single-pass accuracy (i.e., less than about 99%). In another aspect, the disclosed methods are further compatible with counting applications through the incorporation of UID, MID, or a combination thereof.

According to one embodiment, the present disclosure relates to the generation of modular combinatorial nucleic acid tags. The tags are not limited to use any particular nucleic acid sample. For example, a nucleic acid sample can include nucleic acid fragments characterized by of a variety of lengths, length distributions, sequence complexities, and the like. The present disclosure further provides for methods including the attachment of asymmetric modular nucleic acid tags to both ends of a double-stranded target nucleic acid. The tags can include UID, SID, or a combination thereof. In some embodiments, the nucleic acid sample including the one or more target nucleic acids is fragmented prior to attachment of the modular nucleic acid tags. The degree to which a given sample is fragmented can vary. For example, the tags can be attached to highly fragmented DNA samples, such as cell-free DNA, including circulating tumor DNA and cell-free fetal DNA. The resulting library material can be amplified exponentially and retain quantitative information, especially if amplified after concatenation with unique molecular ID sequences.

Figure 1A:
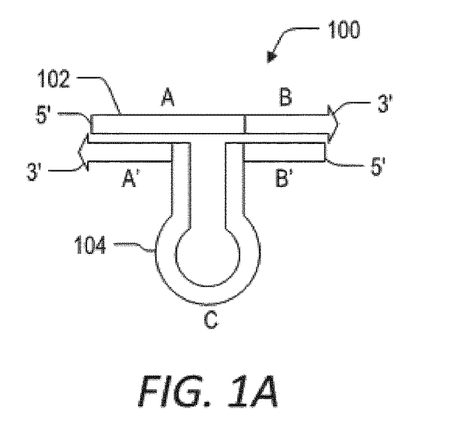
FIG. 1A is schematic illustration of a first example of a modular nucleic acid tag according to the present disclosure.

Turning now to FIG. 1A, an embodiment of a modular and combinatorial nucleic acid tag 100 includes a first strand 102 and a second strand 104. The first strand 102 includes a plurality of segments, including a segment A defining a 5' end of the first strand 102, and a segment B defining a 3' end of the first strand 102. The second strand 104 includes also includes a plurality of segments, including a segment B' defining a 5' end of the second strand 104 and complementary to the segment B of the first strand 102, a segment A' defining a 3' end of the second strand 104 and complementary to the segment A of the first strand 102, and a segment C intermediate the segment A' and the segment B'. The segment A and the segment A' form a first module or A/A' segment pair, whereas the segment B and the segment B' form second module or B/B' segment pair.

Each of the A/A' segment pair and the B/B' segment pair define an identifier sequence. The identifier sequence can be a UID, and SID, another category of identifier sequence, or a combination thereof. The segment C does not contribute to a segment pair, but instead individually define an asymmetric identifier sequence. The asymmetric identifier sequence can contribute to an identifier sequence defined by the A/A' segment pair or the B/B' segment pair, or define a standalone UID, or another identifier sequence. Following attachment of a tag comprising a segment C to a target nucleic acid, the tagged target nucleic acid can be replicated, for example, via polymerase chain reaction. The resulting double-stranded nucleic acid product will include both a copy and a complement of the segment C. As a result, the first and second strands of the original template are identifiable as having been paired. This information can facilitate the application of a variety of different analytical techniques to the resulting sequencing data as will be appreciated by one of ordinary skill in the art.

In one aspect, each of the segments (i.e., A, A', B, B', and C) or segment pairs (i.e., A/A', B/B') are selected from a set of segments or segment pairs having different nucleic acid sequences. For example, the A/A' segment pair can be selected from a first pool of nucleic acid segment pairs, where each member of the first pool of nucleic acid segment pairs has a different sequence. The B/B' segment pair can similarly be selected from a second pool of nucleic acid segment pairs, where each member of the second pool of nucleic acid segment pairs has a different sequence. In one aspect, the first pool of nucleic acid segment pairs and the second pool of nucleic acid segment pairs can be designed to include different sequences such that there is no overlap between the first pool and the second pool. In one aspect, the segment pairs are characterized by a pairwise edit distance of at least 3. In another aspect, each of the segment pairs can be designed to have a defined sequence with a length of at least 10 nucleotides. From this, it will be appreciated that the overall design of a nucleic acid tag therefore has a modular design including at three modules or parts: a first segment pair (e.g., A/A' segment), a second segment pair (e.g., B/B' segment) and an unpaired segment (e.g., segment C). The modular nucleic acids tags are further described as modular and combinatorial in the sense that each segment or segment pair can be selected from a finite set of different segments or segment pairs as described above.

Figure 1B:
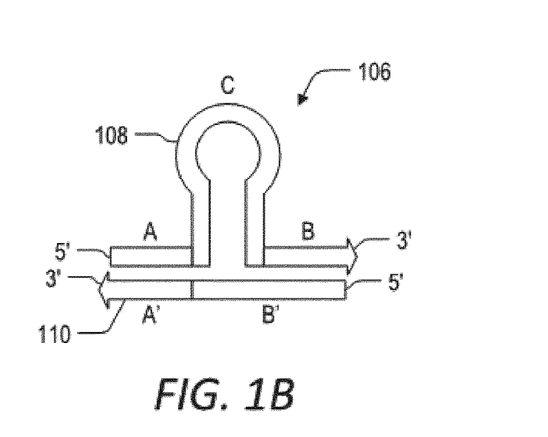
FIG. 1B is schematic illustration of a second example of a modular nucleic acid tag according to the present disclosure.

With continued reference to FIG. 1A, it will be appreciated that the elements of the nucleic acid tag 100 are not necessarily drawn to scale or illustrated showing proper alignment of the nucleic acid segments as will be appreciated from the description below. For example, the element A and the element A' can be designed to have the same length in nucleotides, whereas FIG. 1A illustrates the segment A as having a length greater than the length of the segment A'. Moreover, it will be appreciated that in some embodiments, a nucleic acid tag can include a segment C intermediate the segment A and the segment B instead of, or in addition to a segment C intermediate the segment A' and the segment B'. For example, FIG. 1B illustrates another embodiment of a nucleic acid tag 106 that includes a first strand 108 and a second strand 110. The first strand 108 includes a segment A defining a 5' end of the first strand 108, a segment B defining a 3' end of the first strand 108, and a segment C intermediate the segment A and the segment B. The second strand 110 includes a segment B' defining a 5' end of the second strand 110 and complementary to the segment B of the first strand 108, and a segment A' defining a 3' end of the second strand 110 and complementary to the segment A of the first strand 108. In still another embodiment, a modular nucleic acid tag can exclude a segment C altogether as shown, for example, in FIG. 2A and FIG. 2B.

Notably, the segment C occurs on only one of the two strands of the nucleic acid tags 100 and 106. In these embodiments, the segment C enables directional labeling of a target nucleic acid, asymmetric labeling of a target nucleic acid, or a combination thereof. Accordingly, the segment C can facilitate the final assembly of the sequenced target nucleic acid by embedding both directional and quantitative information in the resulting sequencing data. In one aspect, the segment C can have a random sequence, a defined sequence, or a partially defined sequence.

Figure 1C:
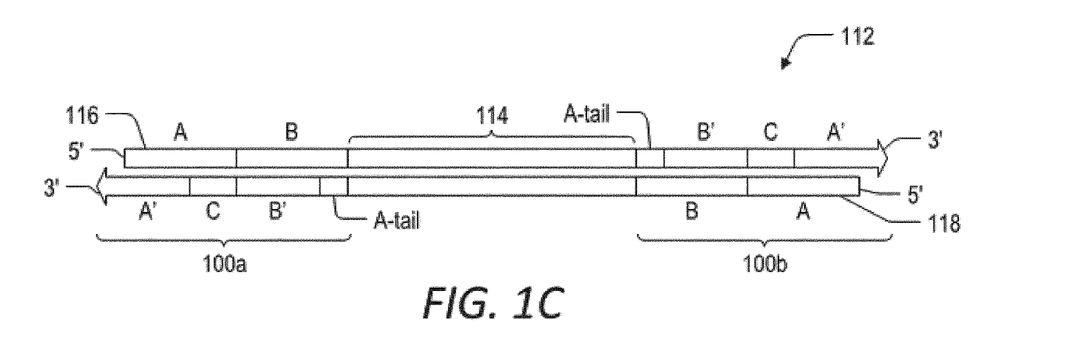
FIG. 1C is schematic illustration of a first example of a doubly-tagged target nucleic acid according to the present disclosure.
Figure 1D:
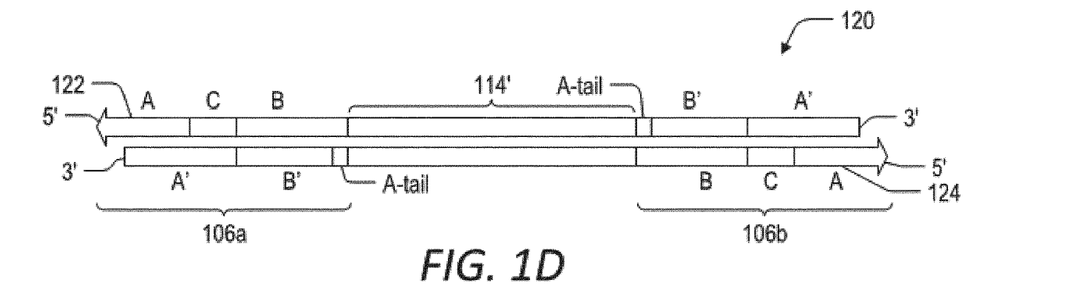
FIG. 1D is schematic illustration of a second example of a doubly-tagged target nucleic acid according to the present disclosure.

Turning now to FIG. 1C and FIG. 1D, a nucleic acid tag can be attached to a target nucleic acid fragment to provide a doubly-tagged target nucleic acid. Referring first to FIG. 1C, a doubly-tagged target nucleic acid 112 includes a double-stranded target nucleic acid fragment or insert 114, a first nucleic acid tag 100a attached to a first end of the insert 114, and a second nucleic acid tag 100b attached to an opposing second end of the insert 114. Notably, each of the tag 100a and the tag 100b comprises an overall structure, including segments A, A', B, B' and C, comparable to the nucleic acid tag 100 in FIG. 1A. With continued reference to FIG. 1C, the tags 100a and 100b are selected from a pool of different modular nucleic acid tags. Accordingly, the tag 100b can include one or more differences in the overall sequence compared with the tag 100a. Put another way, the tag 100a can be characterized as having less than 100% sequence identity to the tag 100b.

In one aspect, each of the tags 100a and 100b are attached to the insert 114 using a ligation-based approach. For example, the FIG. 1C illustrates the use of T/A overhangs to provide sticky ends for enzymatic ligation; however, it will be appreciated that any suitable method can be used to attach one or more tags to an insert. In the illustrated embodiment, the insert 114 is first prepared as a blunt-ended fragment, followed by an A-tailing reaction to provide each strand of the insert 114 with a 3' single A (i.e., an adenine nucleotide) overhang. Each of the tag 100a and the tag 100b are provided with 3' single T (i.e., a thymine nucleotide) overhang on at least one of the two strands of each of the tags 100a and 100b, thereby providing the tags 100a and 100b with ends that are compatible with the insert 114. As noted above, yet other approaches for attaching tags to an insert can be implemented according to the present disclosure. Other example of attachment include blunt cloning, formation of compatible ends other than T/A overhangs (e.g., through the use of restriction enzymes, uracil-directed cleavage), and the like.

In one aspect, one or more of the insert 114 and the tags 100a and 100b can be designed or treated to prevent self-ligation (i.e., ligation of a first tag to a second tag, or ligation of a first insert to a second insert). One method to prevent self-ligation includes selective phosphorylation, whereby one or more terminal nucleotides are dephosphorylated or allowed to remain in an unphosphorylated state. Another approach to limit unwanted ligation events includes the addition of a 5' or 3' overhang at one end of a tag. The overhang can be greater than 1, 2, 3, 4, 5, or 10 nucleotides in length. In one example, the overhang can include three consecutive cytosine nucleotides directly following a uracil nucleotide. In this example, following ligation of the opposing end of the tag to the insert, the tag can be treated (e.g., with uracil deglycosylase and endonuclease IV) to generate tag end compatible for ligation. Yet another method to prevent unwanted ligation events includes the introduction of one or more uracil nucleotides into the tag sequence followed by a sequence that terminates with a modified nucleotide capable of preventing ligation. Non-limiting examples of modified nucleotides include 3' dideoxynucleotides, 5' nucleotides modified with a three carbon (C3) spacer, a 5' cap, the like, and combinations thereof. Following ligation of a tag to the insert, the tag can be treated (e.g., with uracil deglycosylase and at least one of endonuclease VIII and endonuclease IV) to generate tag ends capable of participating in a ligation reaction.

In the case of the doubly-tagged target nucleic acid 112, the 3' region of each the first strand 116 and the second strand 118 includes additional unpaired sequence in the form of the segment C. By comparison, FIG. 1D illustrates an alternative embodiment in which this scheme reversed. Referring first to FIG. 1D, a doubly-tagged target nucleic acid 120 includes the double-stranded target nucleic acid insert 114', a first nucleic acid tag 106a attached to a first end of the insert 114', and a second nucleic acid tag 106b attached to an opposing second end of the insert 114'. Notably, the tag 106a and the tag 106b comprise an overall structure, including segments A, A', B, B', and C, comparable to the nucleic acid tag 106 in FIG. 1B. With continued reference to FIG. 1D, the tags 106a and 106b are selected from a pool of different modular nucleic acid tags. Accordingly, the tag 106b can include one or more differences in the overall sequence compared with the tag 106a. Put another way, the tag 106a can be characterized as having less than 100% sequence identity to the tag 106b.

In addition to the embodiments illustrated in FIGS. 1C and 1D, it will be appreciated that a plurality of different tags can be attached to an insert. For example, a first tag having the structure of the tag 100 can be applied to the first end of an insert while a second tag having the structure of the tag 106 can be applied to an opposing second end of the insert. Still other combinations of tags and inserts can be prepared as would be understood by one of ordinary skill in the art.

As discussed above, the tags (e.g., the tag 100a and tag 100b) can facilitate the final assembly of the sequenced target nucleic acid by embedding both directional and quantitative information in the resulting sequencing data. For example, following amplification and sequencing of the doubly-tagged target nucleic acid 112, a plurality of reads will be generated from amplification products derived from the first strand 116 and the second strand 118. Each of the reads generated from the first strand 116 will include the same unique sequence derived from the combination of the segments A and B from the first tag 100a and the segments A', B' and C from the second tag 100b. By comparison, each of the reads generated from the second strand 118 will include a different unique sequence derived from the combination of the segments A and B from the second tag 100b and the segments A', B' and C from the first tag 100a. Notably, the segments A and B from the first tag 100a are complementary to the segments A' and B' from the first tag 100a, and the segments A and B from the second tag 100b are complementary to the segments A' and B' from the second tag 100b. However, the each of the first strand 116 and the second strand 118 are associated with a different segment C. In one aspect, the segment C of the first tag 100a is different from (i.e., neither complementary nor identical to) the segment C of the second tag 100b. Accordingly, by identify all sequencing reads having the unique combination of segments associated with the first strand 116, it is possible to deduplicate the sequencing data, for example, to enable counting or quantification of the abundance of the insert 114.

In another aspect, amplification of the doubly-tagged target nucleic acid 112 will result in products having a combination of the sequences selected from the first tag 100a or a complement thereof, the second tag 100b or a complement thereof, and the segment C from the first tag 100a or the second tag 100b or a complement thereof. For example, a complementary strand derived from the first strand 116 will include from 5' to 3', from the second tag 100b: i) the segment A, ii) a complement of the segment C, and iii) the segment B, the insert 114, and from the first tag 100a: i) the segment B', ii) the segment C, and iii) the segment A'. Accordingly, sequencing reads derived from the first strand 116 and complements thereof as well as reads derived from the second strand 118 or complements thereof can unambiguously be grouped together to enable consensus analysis. In general, it will be appreciated that a tag as disclosed herein facilitates downstream deduplication and consensus analysis of sequencing data derived from doubly-tagged target nucleic acids. For example, the tagging of a target nucleic acid with at least one segment C can enable proper assembly of complementary sequences during sequencing data analysis, thereby facilitating consensus sequencing from complementary nucleic acid strands of the target nucleic acid.

Figure 2A:
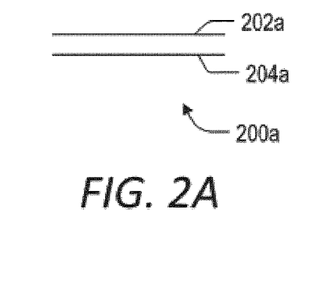
FIG. 2A is a schematic illustration of an example of a modular nucleic acid tag excluding a segment C according to the present disclosure.
Figure 2B:
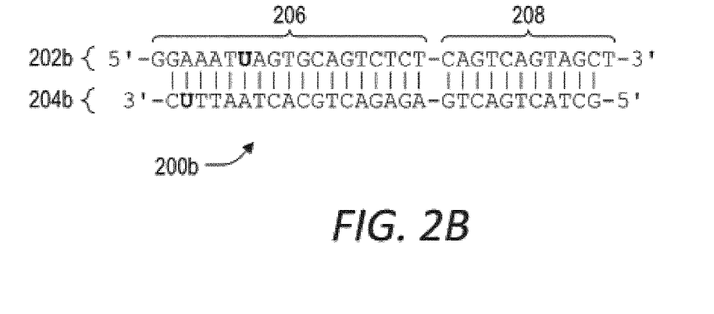
FIG. 2B is an alternative representation of the modular nucleic acid tag of FIG. 2A detailing an example nucleic acid sequence for each strand of the modular nucleic acid tag.

As illustrated in FIGS. 2A-2F, a wide variety of nucleic acid tags are suitable for use according to the present disclosure. In the example shown in FIG. 2A, a tag 200a excludes a segment C altogether. Accordingly, neither the first strand 202a of the tag 200a nor the second strand 204a of the tag 200a includes a hairpin or unpaired loop. Turning to FIG. 2B, the tag 200b includes a first strand 202b having the sequence:

```
                                         (SEQ ID NO: 1)
     GGAAATUAGTGCAGTCTCTCAGTCAGTAGCT,
``` and a second strand 204b having the sequencing:

```
                                         (SEQ ID NO: 2)
     GCTACTGACTGAGAGACTGCACTAATTUC.
```

The tag 200b includes an A/A' segment pair 206 consisting of a 5' portion of the first stand 202b (i.e., segment A) and a 3' portion of the second strand 204b (i.e., segment A'). The tag 200b further includes and a B/B' segment pair 208 consisting of a 3' portion of the first stand 202b (i.e., segment B) and a 5' portion of the second strand 204b (i.e., segment B'). Notably, the tag 200b has the same overall structure as the tag 200a in FIG. 2A, and further illustrates that neither the first strand 202b nor the second strand 202b includes a hairpin or unpaired loop. It will be appreciated that the first strand 202b includes a 5' single G overhang and 3' single T overhang, each of which is unpaired; however, the tag 200b includes no intervening unpaired sequence intermediate the A/A' segment pair 206 and the B/B' segment pair 208.

In addition to the tags illustrated in FIG. 2A and FIG. 2B, a tag according to the present disclosure can include a segment C defining a hairpin, an unpaired loop, or a combination thereof. In the case that the segment C includes an unpaired loop, the sequence defining the unpaired loop can be a defined sequence, a random sequence, or a combination thereof.

Figure 2C:
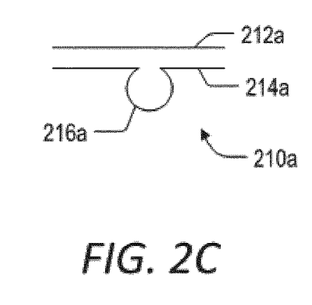
FIG. 2C is a schematic illustration of a modular nucleic acid tag including a segment C defining an unpaired loop according to the present disclosure.
Figure 2D:
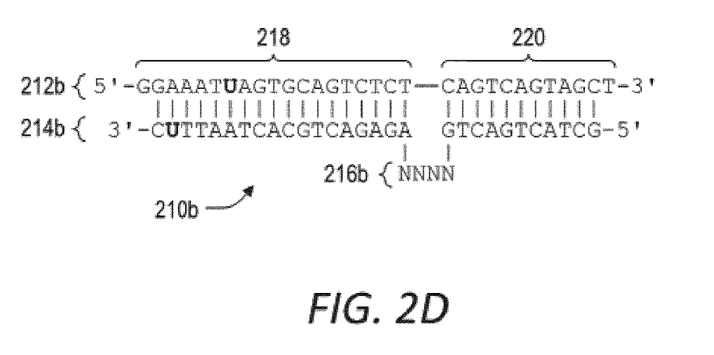
FIG. 2D is an alternative representation of the modular nucleic acid tag of FIG. 2A detailing an example nucleic acid sequence for each strand of the modular nucleic acid tag.

With reference to FIG. 2C, a tag 210a includes a first strand 212a and a second strand 214a. The second strand 214a includes an unpaired loop 216a. Turning to FIG. 2D, the tag 210b includes a first strand 212b having the sequence:

(SEQ ID NO: 1)
GGAAATUAGTGCAGTCTCTCAGTCAGTAGCT, and a second strand 214b having the sequencing:

(SEQ ID NO: 3)
GCTACTGACTGNNNNAGAGACTGCACTAATTUC.

The tag 210b includes an A/A' segment pair 218 consisting of a 5' portion of the first stand 212b (i.e., segment A) and a 3' portion of the second strand 214b (i.e., segment A'). The tag 210b further includes and a B/B' segment pair 220 consisting of a 3' portion of the first stand 212b (i.e., segment B) and a 5' portion of the second strand 214b (i.e., segment B'). Notably, the tag 210b has the same overall structure as the tag 210a in FIG. 2C, and further illustrates that the second strand 212b includes an unpaired loop 216b intermediate the A/A' segment pair 218 and the B/B' segment pair 220. The unpaired loop 216b consists of four consecutive nucleotides (i.e., "NNNN") that neither exhibit intramolecular pairing within the second strand 214b nor intermolecular pairing with the second strand 212b. As in the case of the tag 200b in FIG. 2B, it will be appreciated that the first strand 212b of the tag 210b includes a 5' single G overhang and 3' single T overhang, each of which is unpaired. however, the tag 210b includes no intervening unpaired sequence intermediate the A/A' segment pair 206 and the B/B' segment pair 208.

Figure 2E:
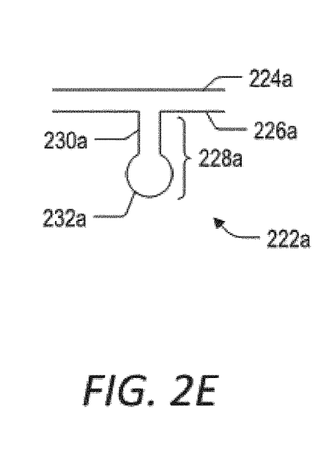
FIG. 2E is a schematic illustration of a modular nucleic acid tag including a segment C defining a hairpin and an unpaired loop according to the present disclosure.
Figure 2F:
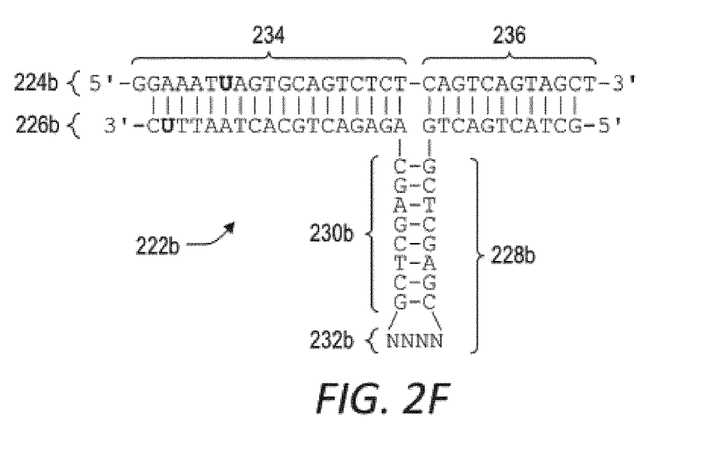
FIG. 2F is an alternative representation of the modular nucleic acid tag of FIG. 2A detailing an example nucleic acid sequence for each strand of the modular nucleic acid tag.

Turning next to FIG. 2E, a tag 222a includes a first strand 224a and a second strand 226a. The second strand 226a includes both a hairpin 230a and an unpaired loop 232a defining a C segment 228a. Turning to FIG. 2F, the tag 222b includes a first strand 224b having the sequence:

(SEQ ID NO: 1)
GGAAATUAGTGCAGTCTCTCAGTCAGTAGCT, and a second strand 226b having the sequencing:

(SEQ ID NO: 4)
GCTACTGACTGGCTCGAGCNNNNGCTCGAG

CAGAGACTGCACTAATTUC.

The tag 222b includes an A/A' segment pair 234 consisting of a 5' portion of the first stand 224b (i.e., segment A) and a 3' portion of the second strand 226b (i.e., segment A'). The tag 222b further includes and a B/B' segment pair 236 consisting of a 3' portion of the first stand 224b (i.e., segment B) and a 5' portion of the second strand 226b (i.e., segment B'). The tag 222b further includes and a C segment 228b including a hairpin 230b and an unpaired loop 232b. Notably, the tag 222b has the same overall structure as the tag 222a in FIG. 2E, and further illustrates that the second strand 226b includes the C segment 228b intermediate the A/A' segment pair 234 and the B/B' segment pair 236. The hairpin 230b consists of two complementary groups of eight nucleotides that exhibit intramolecular pairing within the second strand 226b. The unpaired loop 232b consists of four consecutive nucleotides (i.e., "NNNN") that neither exhibit intramolecular pairing within the second strand 226b nor intermolecular pairing with the second strand 226b. As in the case of the tag 200b in FIG. 2B, it will be appreciated that the first strand 224b of the tag 222b includes a 5' single G overhang and 3' single T overhang, each of which is unpaired.

In one aspect, each segment of a modular nucleic acid tag can be assembled from one or more subunits. For example, a segment can include a single subunit or a plurality of subunits concatenated together. Accordingly, individual subunits can be selected from in a combinatorial manner based on a number of factors including the selected sequencing platform, the type of sample to be sequenced, and the like.

In another aspect, the modular nucleic acid tag can include a sample identifier or SID. In this case, modular nucleic acid tags having the same SID can be added to each of the target nucleic acid fragments in a given sample. Alternatively, modular nucleic acid tags including two or more different SID sequences can be added to each of the target nucleic acid fragments in a given sample. In the case that more than one SID is employed per target nucleic acid sample, the modular nucleic acid tag can include a combination of an SID/MID and a UID in order to increase the combinatorial power of the overall nucleic acid tag sequence.

As discussed above, in some embodiments, a nucleic acid tag can include one or more modification to prevent ligation of a tag end, enable the creation of tag ends capable of ligation, or a combination thereof. With reference to FIG. 2B, a 5' end of the first strand 202b includes, from 5' to 3', a single guanine nucleotide overhang, 5 standard nucleotides, and a uracil nucleotide. In this example, the terminal guanine nucleotide can include a 3-carbon spacer to prevent ligation of the corresponding end of the tag 200b to another molecule. In another aspect, a 3' end of the second strand 204b includes, from 3' to 5', a single cytosine nucleotide, and a uracil nucleotide. The terminal cytosine nucleotide can be provided as a dideoxycytosine nucleotide to further prevent ligation of the corresponding end of the tag 200b to another molecule. By contrast an opposing end of the tag 200b can be phosphorylated to promote ligation of that end (i.e., the 5' end of the second strand 204b). Following ligation of the tag 200b to an insert, the tag 200b can be treated with uracil deglycosylase and an endonuclease. The treatment will ultimate target the aforementioned uracil nucleotides at the 5' end of the first strand 202b and the 3' end of the second strand 204b, thereby forming a 3' overhang with in the A/A' segment pair 206 that can participate in a ligation with another suitable molecule, such as another doubly-tagged nucleic acid insert or a universal nucleic acid adapter (e.g., a forked adapter or a hairpin adapter) compatible with the selected sequencing platform. The tag 210b in FIG. 2D and the tag 222b in FIG. 2F can be designed to include similar modifications as indicated by the bolded uracil nucleotides.

Example

As a proof of principle in assembling the modular nucleic acid tags, PCR amplicons of 116 bp of KRAS Exon 3 were generated from TruQ1 reference human gDNA (HORIZON DISCOVERY GROUP) with Q5 DNA polymerase (NEW ENGLAND BIOLABS). The product was purified with an AMPure PCR purification kit (BECKMAN COULTER) and verified using both an AGILENT Bioanalyzer micro-capillary based electrophoresis system and denaturing gels. A 3' overhang dA was added to the amplicons using Taq DNA polymerase (NEW ENGLAND BIOLABS). Oligodeoxynucleotides containing uracil with sequences illustrated by FIGS. 2D and 2F were obtained and purified. The oligodeoxynucleotides were annealed after the stoichiometry was determined by measuring each sequence-specific extinction coefficient and sample absorption in the UV range. The annealed oligonucleotide complex was added to the A-tailed KRAS insert at 25:1::Oligo complex:insert ratio and the mixture was treated with T4 DNA Ligase at 37° C. for 30 min. The resulting material was cleaved using antarctic uracil deglycosylase (UDG) and endonuclease IV at 37° C. for 30 min. The samples were purified with an AMPure PCR purification kit (BECKMAN COULTER) at 2× volume. The eluate was ligated using T4 DNA ligase in 15% PEG6000. The ligation products were examined using denaturing gels.

The invention claimed is:

1. A method of preparing a library of nucleic acids having modular end sequences, wherein the method comprises the following steps:
   (a) combining a pool of different modular nucleic acid tags with a nucleic acid sample, wherein the nucleic acid sample includes a plurality of double-stranded target nucleic acids;
   (b) joining the ends of each of the double-stranded target nucleic acids to tags selected from the pool of different modular nucleic acid tags, thereby forming a plurality of doubly-tagged target nucleic acids;
   (c) amplifying each of the doubly-tagged target nucleic acids, thereby preparing a library of nucleic acids having modular end sequences; and
   (d) detecting the library of amplified nucleic acids having modular end sequences,
       wherein each of the different modular nucleic acid tags has a first strand and a second strand,
       wherein the first strand includes: (i) a segment A defining a 5' end of the first strand, and (ii) a segment B defining a 3' end of the first strand,
       wherein the second strand includes: (i) a segment B' defining a 5' end of the second strand and complementary to the segment B of the first strand, and (ii) a segment A' defining a 3' end of the second strand and complementary to the segment A of the first strand,
       wherein each of the different modular nucleic acid tags includes a hairpin segment C positioned intermediate of the segment A and the segment B,
       wherein each of the segments A, A', B, B', and C are selected from a set of segments having different nucleic acid sequences,
       wherein each segment of the set of segments has a defined sequence of at least 10 nucleotides, and
       wherein the set of segments is characterized by a pairwise edit distance of at least 3.

2. The method of claim 1, wherein each of the different modular nucleic acid tags further includes at least one strand cleavage site.

3. The method of claim 2, further comprising contacting the doubly-tagged target nucleic acids with a cleavage agent to cleave the doubly-tagged target nucleic acid at the cleavage sites, thereby forming cleaved doubly-adapted target nucleic acids.

4. The method of claim 1, further comprising concatenating the doubly-tagged target nucleic acids, thereby forming concatenated doubly-tagged target nucleic acids.

5. The method of claim 4, further comprising joining the ends of each of the concatenated doubly-tagged target nucleic acids with an adapter, thereby forming a plurality of doubly-adapted concatemers.

6. The method of claim 5, further comprising amplifying each of the doubly-adapted concatemers.

7. The method of claim 1, wherein joining to the modular nucleic acid tag is by ligation.

8. The method of claim 3, wherein the strand cleavage site comprises one or more deoxyuracils, and the cleavage agent comprises Uracil-DNA-N-glycosylase (UNG) and an endonuclease, wherein the endonuclease is Endonuclease IV.

9. The method of claim 3, wherein the cleavage site comprises one or more abasic sites, and wherein the cleavage agent comprises Endonuclease IV.

10. The method of claim 1, wherein each of the different modular nucleic acid tags further comprises a punctuation sequence, the punctuation sequence including at least three blocks, each of the blocks consisting of a homopolymer of at least three identical nucleotides.

11. The method of claim 1, further comprising the following steps after step (d):
    (e) sequencing the library of amplified nucleic acids having modular end sequences, thereby generating a plurality of sequencing reads; and
    (f) analyzing the plurality of sequencing reads by at least one of: (i) deduplicating the plurality of sequencing reads, and (ii) determining a consensus sequence.

* * * * *

SEQUENCE LISTING

<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: Single stranded

<400> SEQUENCE: 1
ggaaattagt gcagtctctc agtcagtagc t                                      31

<210> SEQ ID NO 2
<211> LENGTH: 29
<212> TYPE: DNA
<213> ORGANISM: Artificial Sequence
<220> FEATURE:
<223> OTHER INFORMATION: Single stranded

<400> SEQUENCE: 2
gctactgact gagagactgc actaatttc                                         29

<210> SEQ ID NO 3
<211> LENGTH: 33
<212> TYPE: DNA
<213> ORGANISM: Artificial Sequence
<220> FEATURE:
<223> OTHER INFORMATION: Single stranded
<220> FEATURE:
<221> NAME/KEY: misc_feature
<222> LOCATION: (12)..(15)
<223> OTHER INFORMATION: n is a, c, g, or t

<400> SEQUENCE: 3
gctactgact gnnnnagaga ctgcactaat ttc                                    33

<210> SEQ ID NO 4
<211> LENGTH: 49
<212> TYPE: DNA
<213> ORGANISM: Artificial Sequence
<220> FEATURE:
<223> OTHER INFORMATION: Single stranded
<220> FEATURE:
<221> NAME/KEY: misc_feature
<222> LOCATION: (20)..(23)
<223> OTHER INFORMATION: n is a, c, g, or t

<400> SEQUENCE: 4
gctactgact ggctcgagcn nnngctcgag cagagactgc actaatttc                   49